(12) United States Patent
Kwon et al.

(10) Patent No.: US 10,532,822 B2
(45) Date of Patent: Jan. 14, 2020

(54) GAS-FLAMMABILITY SENSING SYSTEMS AND METHODS

(71) Applicant: The Boeing Company, Chicago, IL (US)

(72) Inventors: Eddie Kwon, Seattle, WA (US); Jason Scott Damazo, Seattle, WA (US); Philipp Andreas Boettcher, Philadelphia, PA (US); William J. Sweet, Seattle, WA (US); Kevin Richard Housen, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 86 days.

(21) Appl. No.: 15/415,673

(22) Filed: Jan. 25, 2017

(65) Prior Publication Data
US 2018/0208324 A1 Jul. 26, 2018

(51) Int. Cl.
*B64D 37/32* (2006.01)
*G01N 25/52* (2006.01)
*G01N 31/12* (2006.01)

(52) U.S. Cl.
CPC .............. *B64D 37/32* (2013.01); *G01N 25/52* (2013.01)

(58) Field of Classification Search
CPC .......................... G01N 2027/222; G01N 25/52
See application file for complete search history.

(56) References Cited

U.S. PATENT DOCUMENTS

| | | | | |
|---|---|---|---|---|
| 3,999,936 A | * | 12/1976 | Hasselmann | B67D 7/0476 431/202 |
| 4,115,235 A | * | 9/1978 | Capone | G01N 1/24 204/409 |
| 4,348,888 A | * | 9/1982 | Snee | G01N 31/12 422/98 |
| 5,053,200 A | * | 10/1991 | Schaeffer | G01N 1/2258 138/42 |
| 2016/0123860 A1 | * | 5/2016 | McBrien | G01F 1/00 702/25 |

(Continued)

OTHER PUBLICATIONS

Schmidt et al., "Dielectric Permittivity of Eight Gases Measured with Cross Capacitors," International Journal of Thermoplastics, vol. 24, No. 2, Mar. 2003.

*Primary Examiner* — Daniel S Larkin
(74) *Attorney, Agent, or Firm* — Dascenzo Intellectual Property Law, P.C.

(57) ABSTRACT

Gas-flammability sensing systems and methods may be used to determine the flammability of gas mixtures in measurement volumes such as a fuel tank (e.g., an aircraft fuel tank). Gas-flammability sensing systems include a test cell structured to receive a gas sample, a heater in thermal communication with the test cell, and a gas meter configured to measure a physical property of the gas sample within the test cell related to the combustion state of the gas sample. The heater is configured to heat the gas sample to an elevated temperature less than the autoignition temperature of the gas sample. Methods of determining the flammability of a gas sample include collecting the gas sample, heating the gas sample to the elevated temperature, measuring the physical property of the gas sample after heating, and determining the flammability of a gas sample based upon the measured physical property.

38 Claims, 4 Drawing Sheets

(56) References Cited

U.S. PATENT DOCUMENTS

2018/0024105 A1* 1/2018 Damazo ................ G01N 33/22
                                                              436/126
2018/0074036 A1* 3/2018 Boettcher ............ G01N 33/227

* cited by examiner

GAS-FLAMMABILITY SENSING SYSTEMS AND METHODS

FIELD

The present disclosure relates to gas-flammability sensing systems and methods.

BACKGROUND

The effective control of flammable gases, especially flammable gases in confined spaces, is important in many contexts. For example, fuel tanks for liquid fuel will develop a fuel vapor mixture in the ullage space of the fuel tank. If the vapor mixture includes a suitable amount of fuel and oxidant (such as molecular oxygen supplied in air), the vapor mixture may be flammable. Large fuel tanks may be found in large vehicles, such as aircraft and ships, and may be found at storage facilities. In addition to liquid fuel storage, transport, and use, flammable gas mixtures may be a consideration in chemical processing, oil refining, mining, power production, heating, metal fabrication, and operations which involve combustible particulate such as sawdust, metal, flour, and grain. In some contexts, one may want to verify that an environment is not flammable and/or whether a gas mixture is flammable Various sensors may be used to detect potentially flammable gas mixtures. These sensors generally fall into one of four categories: (1) catalytic combustion sensors, (2) infrared absorption sensors, (3) flame ionization sensors, and (4) oxygen sensors. Catalytic combustion sensors include catalysts to encourage combustion reactions. Degradation of the catalysts is significant and causes catalytic combustion sensors to be inaccurate or to need persistent calibration. Infrared absorption sensors monitor specific wavelengths of light associated with optical absorption of known flammable gas components (e.g., a fuel molecule). If the gas composition is complex (having may molecular species) and/or if there are several varying species, the infrared absorption spectra may be difficult to reliably interpret. Flame ionization sensors mix a gas sample with a known amount of flammable gas and ignite the mixture with a pilot flame. Use of flammable gas and a pilot flame limits the applicability of flame ionization sensors to situations in which the hazards of the sensor can be isolated from the gas being tested. Oxygen sensors may incorporate high temperature zirconia sensors that may pose an ignition hazard in flammable mixtures due to the temperature of the zirconia. Other types of oxygen sensors incorporate optical detection via a luminescent probe sensitive to the concentration of oxygen. Luminescent probes may degrade, causing limitations similar to catalytic combustion sensors. Complex mixtures may cause artifacts or otherwise interfere with the luminescent probes. Yet other types of oxygen sensors incorporate electro-galvanic fuel cell sensors that have an electrode that is rapidly consumed by exposure to oxygen.

One method to minimize the risk of a flammable environment in the ullage space of a fuel tank is to flush the ullage space with 'inert' gas. This process may be referred to as inerting and may be called inertion. The inert gas is selected to reduce the concentration of oxidant in the ullage space and may not be entirely inert. The inert gas may include oxidant at a low enough concentration that, when mixed with fuel vapor, the mixture is not flammable. Examples of inert gases for fuel tank inertion include nitrogen, nitrogen-enriched air, steam and carbon dioxide. Target oxygen concentrations in the ullage space depend on the fuel constituents (e.g., for jet A fuel, less than 12% (by volume) is considered sufficiently non-flammable). However, in some applications, the oxygen concentration in the ullage space and the flammability of the gas in the ullage space cannot be reliably confirmed because existing flammability sensors are ill-suited. For example, aircraft fuel tanks may hold large quantities of jet fuel and vapor that has a complex assortment of molecular constituents. Additionally, aircraft fuel tanks are subject to a broad range of temperature and pressure conditions. The types, amounts, and concentrations of vaporous fuel species and dissolved gases are affected by temperature and pressure. Therefore, the amount of inert gas needed to achieve the target concentration may vary greatly during a flight.

In conventional aircraft fuel tank inerting systems, the inert gas is substantially continuously supplied to the fuel tank in an effort to maintain the oxygen concentration below the target concentration regardless of the conditions in the fuel tank (e.g., amount of fuel, temperature, pressure). Because the non-flammability of the ullage space cannot be ensured in conventional aircraft fuel tank inerting systems, the aircraft design needs to accommodate the potential for flammable mixtures in the fuel tank (at the likely cost of excess weight, fuel efficiency, and maintenance complexity). Additionally, conventional systems supply gas continuously to the fuel tank, which may lead to increased system capacity needs and increased system wear.

SUMMARY

Gas-flammability sensing systems and methods may be used to determine the flammability of gas mixtures in measurement volumes such as a fuel tank (e.g., an aircraft fuel tank). Gas-flammability sensing systems include a test cell structured to receive a gas sample, a heater in thermal communication with the test cell, and a gas meter configured to measure a physical property (e.g., electrical or optical property) of the gas sample within the test cell related to the combustion state of the gas sample. The heater is configured to heat the gas sample to an elevated temperature less than the autoignition temperature of the gas sample and sufficient to permit thermal reaction of the gas sample. The combustion state may relate to, and the physical property may be affected by, the presence, type, and/or amount of reaction products and/or reaction intermediates in the heated gas sample.

Methods of determining the flammability of a gas sample include collecting the gas sample, heating the gas sample to the elevated temperature, measuring the physical property of the gas sample after heating, and determining the flammability of a gas sample based upon the measured physical property. Methods may include sampling the gas sample from the ullage space of a fuel tank and controlling the concentration of inert gas in the ullage space of the fuel tank based upon the flammability of the gas sample.

DESCRIPTION

Figure 1:
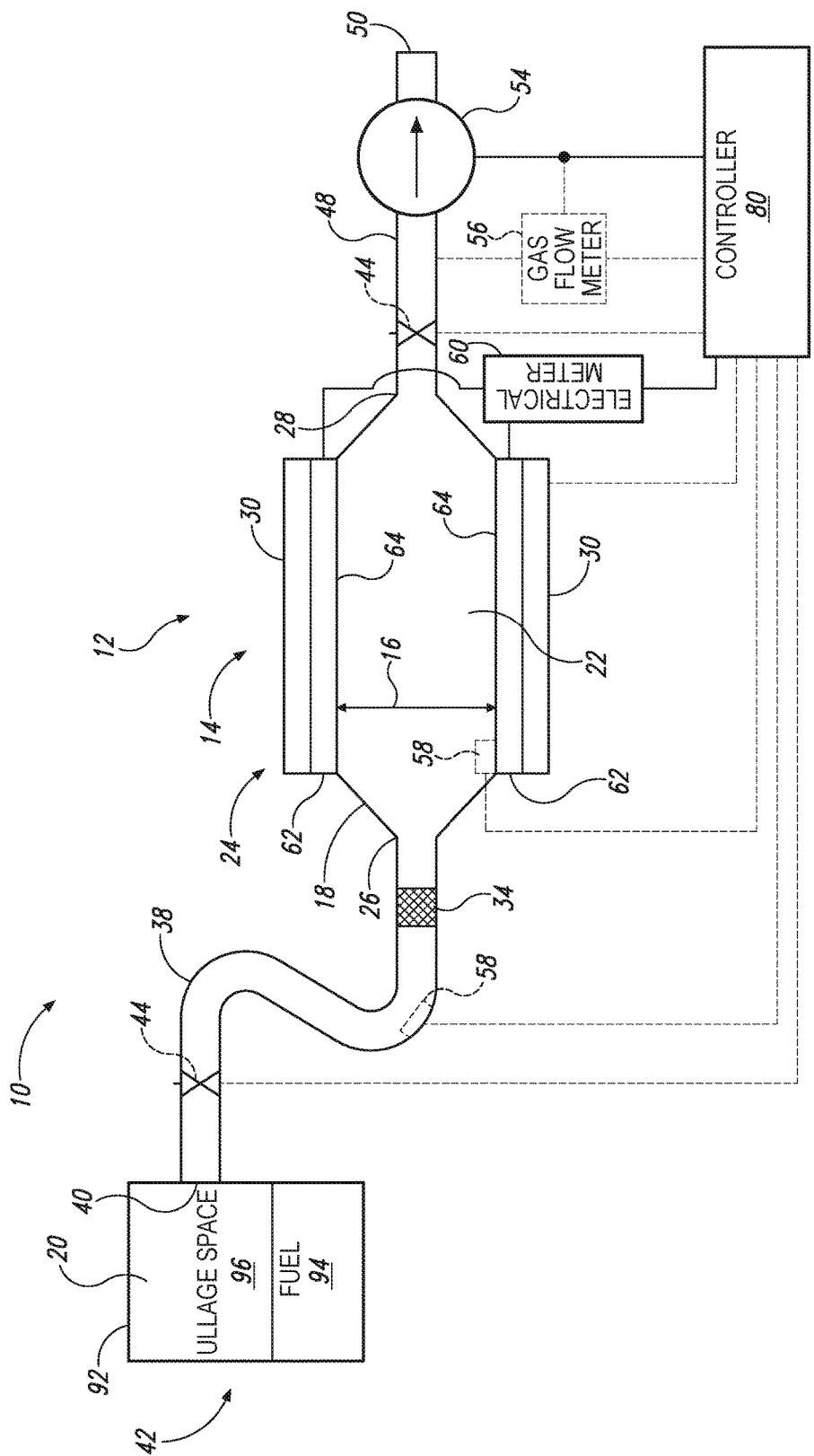
FIG. 1 is a schematic representation of a gas-flammability sensing system according to the present disclosure.

FIGS. 1-7 illustrate systems and methods for gas-flammability sensing. In general, in the drawings, elements that are likely to be included in a given embodiment are illustrated in solid lines, while elements that are optional or alternatives are illustrated in dashed lines. However, elements that are illustrated in solid lines are not essential to all embodiments of the present disclosure, and an element shown in solid lines may be omitted from a particular embodiment without departing from the scope of the present disclosure. Elements that serve a similar, or at least substantially similar, purpose are labelled with numbers consistent among the figures. Like numbers in each of the figures, and the corresponding elements, may not be discussed in detail herein with reference to each of the figures. Similarly, all elements may not be labelled or shown in each of the figures, but reference numerals associated therewith may be used for consistency. Elements, components, and/or features that are discussed with reference to one or more of the figures may be included in and/or used with any of the figures without departing from the scope of the present disclosure.

FIG. 1 is a schematic representation of a gas-flammability sensing system 10 (which also may be referred to as a gas-flammability sensing device). The gas-flammability sensing system 10 is configured to determine whether a gas mixture 20 is flammable without igniting the gas mixture 20 or a sample of the gas mixture 20 (a gas sample 22). The gas-flammability sensing system 10 is configured to supply conditions suitable to cause a flammable gas mixture to thermally react but unsuitable to cause the flammable gas mixture to rapidly combust (e.g., to burn or to explode). The gas-flammability sensing system 10 is configured to measure physical changes (e.g., electrical and/or optical changes) in the gas sample 22 due to the thermal reaction. Physical changes in the gas sample 22 reflect chemical composition changes due to the thermal reaction. Hence, by detecting physical changes, the gas-flammability sensing system 10 may detect whether the gas mixture 20 is flammable and/or the degree or extent of flammability (for flammable or non-flammable mixtures).

The gas-flammability sensing system 10 is configured to receive the gas sample 22 from the gas mixture 20 into a test cell 12, to heat the gas sample 22 to an elevated temperature that is below the autoignition temperature of the gas sample 22 (and below the autoignition temperature of the gas mixture 20), and to measure one or more physical properties (e.g., electrical and/or optical properties) of the heated gas sample 22 with a gas meter 24. The physical properties are related to chemical composition of the heated gas sample 22 and indicate the combustion state of the gas sample 22 at the elevated temperature. The combustion state of the gas sample 22 is the amount of thermal reaction of the gas sample 22. The thermal reaction of the gas sample 22 is the same reaction that may occur during rapid combustion but at a rate and/or to an extent that is less than what occurs in rapid combustion. The combustion state may relate to, and the physical properties may be affected by, the presence, type, and/or amount of reaction products and/or reaction intermediates. The thermal reaction may result in complete combustion and/or partial combustion, and may generate ions and/or other intermediate products during the reaction. For combustion of a hydrocarbon, complete combustion products include water and carbon dioxide; partial combustion products include formaldehyde and carbon monoxide.

For the gas-flammability sensing system 10, the elevated temperature is selected according to the range of gas mixtures 20 that may be sampled. The elevated temperature is selected to be lower than the autoignition temperature of any of the expected gas mixtures 20 that are flammable. At the autoignition temperature or higher, a flammable gas mixture will ignite and rapidly combust without any further energy source needed. Non-flammable gas mixtures do not have an autoignition temperature. However, for clarity in the present disclosure, where an autoignition temperature is undefined (e.g., with respect to a non-flammable mixture), the autoignition temperature is treated as infinite.

The gas sample 22 and the gas mixture 20 are gaseous and may include liquid and solid components (e.g., the gas mixture 20 may include and/or may be an aerosol, a mist, a vapor, and/or a suspension). The gas mixture 20 may be flammable and subject to rapid combustion (e.g., generating a flame, a deflagration, and/or a detonation) in the presence of an ignition source (or at a temperature at least as great as the autoignition temperature). For example, the gas mixture 20 may be a fuel vapor mixture. The gas mixture 20 may be an atmosphere external to the gas-flammability sensing system 10, may be the gas environment in an enclosed space, and/or may be a process gas in an industrial process. The gas mixture 20 is in a measurement volume 42, which may be an open or a closed space. For example, the gas mixture 20 may be in a ullage space 96 of a fuel tank 92 and may include air and fuel vapor. The fuel tank 92 may include fuel 94 as a source of fuel vapor.

The gas mixture 20 generally has combustion fuel and oxidant, though the amounts, relative abundance, and types may be an object of measurement with the gas-flammability sensing system 10. For example, the relative amounts may vary over time and the gas-flammability sensing system 10 may be configured and/or used to monitor changes of the gas mixture 20 (e.g., verifying that the gas mixture 20 remains flammable or non-flammable, and/or detecting when the gas mixture 20 is flammable or non-flammable).

The combustion fuel is a chemical component that will react with the oxidant in a combustion reaction, i.e., an exothermic oxidation-reduction reaction (a redox reaction). Examples of combustion fuels include a hydrocarbon fuel, molecular hydrogen, methane, propane, gasoline, diesel fuel, kerosene, jet fuel, and ethylene. Examples of oxidants include molecular oxygen, nitrous oxide, and hydrogen peroxide.

When the combustion fuel and oxidant are mixed in suitable portions and amounts, the gas mixture 20 may be flammable. Flammable gas mixtures 20 are capable of rapid combustion (e.g., burning) and may support a sustained flame and/or a self-propagating flame front. Rapid combustion occurs when a portion of the gas mixture 20 is heated above the autoignition temperature (e.g., by an ignition source), sufficient heat is generated by the combusting gas mixture 20 to heat surrounding gas, and there is sufficient combustion fuel and oxidant available.

Mixtures of combustion fuel and oxidant are flammable only over a limited range of concentrations called the flammability range or the explosive range. The flammability range is delimited by the lower flammability limit and the upper flammability limit (also called lower and upper explosive limits, or lower and upper ignition limits). Mixtures outside the flammability range are described as too lean to combust (if the combustion fuel concentration is below the lower flammability limit) or too rich to combust (if the combustion fuel concentration is above the upper flammability limit). The flammability range may be affected by the pressure, the density, the type of combustion fuel, the type of oxidant, the presence and type of diluent gas (components that do not participate in reaction), and heat sources or sinks in contact with the gas mixture 20. The autoignition temperature generally varies across the flammability range, with a minimum in the flammability range near the stoichiometric ratio of the combustion fuel and oxidant.

The gas-flammability sensing system 10 includes an inlet 40, an outlet 50, a test cell 12 fluidically connected to the inlet and the outlet, a heater 30 in thermal communication with the test cell 12, and a gas meter 24, as described in more detail below. The test cell 12 is structured to receive the gas sample 22 through the inlet 40 and to discharge the gas sample 22 through the outlet 50. The heater 30 is positioned and configured to heat the gas sample 22 within the test cell 12 to between 50° C. and 500° C. The gas meter 24 is configured to measure a physical property of the gas sample 22 within the test cell 12 related to a combustion state of the gas sample 22 in the test cell 12.

The test cell 12 of the gas-flammability sensing system 10 is structured to receive the gas sample 22 from the measurement volume 42 and to discharge the gas sample 22 from the test cell 12. The test cell 12 defines a probed region 14 (an interior volume of the test cell 12) in which physical properties of the gas sample 22 may be measured.

The probed region 14 generally is relatively thin, defining an open volume with a characteristic sample thickness 16 that is significantly less than transverse dimensions (such as length or width). The sample thickness 16 may also be referred to as the thickness of the probed region 14. The sample thickness 16 may be thin enough to restrict combustion in the gas sample 22. For example, the sample thickness 16 may be thin enough to quench a propagating flame front in the gas sample 22. That is, the sample thickness 16 may be less than the characteristic quenching dimension of the gas sample 22 in the geometry of the probed region 14.

The characteristic quenching dimension is a characteristic measure of a flammable gas in a given set of environmental conditions and confinement conditions. Between parallel plates, the characteristic quenching dimension may be the plate offset distance and may be called the quenching distance and is defined as the smallest distance between the plates that will permit a flame to propagate in flammable gas. In a tube or cylindrical confinement, the characteristic quenching dimension may be the diameter and may be called the quenching diameter and is defined as the smallest diameter of a tube that will permit a flame to propagate in flammable gas. The characteristic quenching dimension generally depends on the composition of the flammable gas mixture. For ease of reference herein, and unless indicated otherwise herein, the characteristic quenching dimension, the quenching distance, and the quenching diameter, when used to describe a combustion fuel generally, indicates the minimum of the respective characteristic quenching parameter, quenching distance, and quenching diameter of a flammable mixture of the combustion fuel and any other given components. For example and as used herein, the quenching distance of ethylene in air is the minimum quenching distance of a flammable mixture of ethylene and air. The minimum values of the characteristic quenching dimension, the quenching distance, and the quenching diameter may be different and may be at different concentrations of combustion fuel. Generally, the minimum value of the characteristic quenching dimension is found close to the stoichiometric concentration of the combustion fuel. As used herein and unless otherwise specified, the characteristic quenching dimensions are specified in standard pressure and temperature conditions (before ignition of the flammable mixture) and without gravitational bias (horizontal flame front).

The sample thickness 16 of the probed region 14 may be less than the characteristic quenching dimension of the combustion fuel at the conditions (e.g., temperature and pressure) relevant to testing the gas mixture 20 (e.g., the conditions of the gas mixture 20 in the measurement volume 42. For example, the sample thickness 16 may be less than the quenching distance of a mixture of the combustion fuel and oxidant, and/or the quenching distance of a mixture of the combustion fuel and air. Suitable sample thicknesses 16 include at most 10 mm, at most 5 mm, at most 2 mm, at most 1 mm, and/or at least 0.1 mm. Selecting the sample thickness 16 near or less than the relevant characteristic quenching dimension may reduce the likelihood for rapid combustion and/or a propagating flame front originating in the test cell 12 that could lead to ignition of the gas mixture 20 in the measurement volume 42.

The gas-flammability sensing system 10 includes the inlet 40, configured to accept the gas sample 22 into the system, and the outlet 50, configured to discharge the gas sample 22 from the system. The inlet 40 is fluidically connected to the measurement volume 42 (e.g., to the ullage space 96) and fluidically connected to the test cell 12, at a test cell inlet 26. In some embodiments, the inlet 40 is the same as the test cell inlet 26. In some embodiments, the inlet 40 and the test cell inlet 26 are separated by an inlet channel 38. The inlet channel 38 may be relatively long to physically isolate the test cell 12 from the measurement volume 42. Physical isolation may be useful for thermal isolation of the test cell 12 and/or for remote monitoring of the measurement volume 42. The inlet channel 38 may include bends such that no straight line path exists between the test cell 12 and the measurement volume 42, for example to prevent hot particle emission from the test cell 12 from entering the measurement volume 42 (and potentially igniting the gas mixture 20 in the measurement volume 42).

The outlet 50 is fluidically connected to the test cell 12, at a test cell outlet 28. In some embodiments, the outlet 50 is the same as the test cell outlet 28. In some embodiments, the outlet 50 and the test cell outlet 28 are separated by an outlet channel 48. The outlet 50 of the gas-flammability sensing system 10 generally is configured to discharge the gas sample 22 after testing in the test cell 12 into a volume other than the measurement volume 42. However, in some embodiments, the gas sample 22 after testing may be discharged into the measurement volume 42. In embodiments where the gas sample 22 after testing is discharged through the outlet 50 into the measurement volume 42, the elevated temperature of the gas sample 22 may be mitigated before discharge into the measurement volume 42 (to avoid potential ignition of the gas mixture 20 in the measurement volume 42).

The gas-flammability sensing system 10 may be configured to collect discrete gas samples 22 (e.g., by operating valves 44) by periodically or episodically loading each gas sample 22 into the test cell 12. Additionally or alternatively, the gas-flammability sensing system 10 may be configured for continuous sampling of the gas mixture 42, for example by permitting gas sample 22 to flow through test cell 12 and/or to flow freely from the inlet 40 to the outlet 50.

The inlet 40, the inlet channel 38, the test cell inlet 26, the outlet 50, the outlet channel 48, and/or the test cell outlet 28 may be associated with one or more valves 44 that are configured to open, close, and/or adjust the gas flow into and/or out of the test cell 12. In the example of FIG. 1, two valves 44 are illustrated, one in the inlet channel 38 (also referred to as a sample valve) and one in the outlet channel 48 (also referred to as an exit valve). One valve 44 may serve as a sample valve and/or an exit valve and may be located at the inlet 40, in the inlet channel 38, at the test cell inlet 26, at the test cell outlet 28, in the outlet channel 48, or at the outlet 50. If valves 44 are located at opposite ends of the test cell 12 (e.g., in the inlet channel 38 and in the outlet channel 48 as shown in the example of FIG. 1), the gas sample 22 may be isolated within the test cell 12 from the measurement volume 42 and any exit volume or external atmosphere. Each valve 44 independently may include, and/or may be, a stop valve, a check valve, a one-way valve, and/or a proportional valve.

The gas-flammability sensing system 10 may include a pump 54 in fluidic communication with the test cell 12 and configured to pump the gas sample 22 (e.g., configured to exhaust the gas sample 22 from the test cell 12 to the outlet 50 and/or to draw the gas sample 22 from the inlet 40 to the test cell 12). The pump 54 may establish a pressure differential between the measurement volume 42 and the test cell 12 (with a lower pressure in the test cell 12), and/or a pressure differential between the test cell 12 and the outlet 50 (with a lower pressure at the outlet 50). Additionally or alternatively, the test cell 12 may have an interior pressure that is less than the pressure in the measurement volume 42 and/or an interior pressure that is greater than the pressure at the outlet 50. Pump 54 may include, and/or may be, a vacuum pump, a fan, a blower, an impeller, a rotary pump, and a reciprocating pump.

The gas-flammability sensing system 10 may include a gas flow meter 56 to measure and/or to monitor the flow of the gas sample 22 into the test cell 12, out of the test cell 12, and/or through the gas-flammable sensing system 10. The gas flow meter 56 and the pump 54 may be used to control and/or regulate the flow of gas in the gas-flammability sensing system 10.

The gas-flammability sensing system 10 is configured to avoid ignition of the gas sample 22 in the test cell 12 and configured to avoid ignition of the gas mixture 20 in the measurement volume 42. Hence, the gas-flammability sensing system 10 has no flame or other ignition source active in the test cell 12 or upstream of the test cell 12 (e.g., in the inlet channel 38). In the gas-flammability sensing system 10, the gas sample 22 is heated to the elevated temperature without exposing the gas sample 22 to an ignition source.

The gas-flammability sensing system 10 may include a flame arrester 34 between the measurement volume 42 and the test cell 12, for example, at the inlet 40, in the inlet channel 38, and/or at the test cell inlet 26. The flame arrester 34 may be a deflagration arrester and/or a detonation arrester. The flame arrester 34 functions by absorbing heat from a flame front passing through the flame arrester 34 to reduce the temperature below the autoignition temperature and consequently extinguishing the flame front. The flame arrester 34 typically includes metal elements (such as mesh, ribbons, wires, and/or particulate) that define small passages for gas flow. Use of the flame arrester 34 may prevent any rapid combustion and/or propagating flame front originating in the test cell 12 from igniting the gas mixture 20 in the measurement volume 42.

The gas-flammability sensing system 10 includes one or more heaters 30. The heaters 30 are configured to heat the gas sample 22. The heaters 30 may be configured to heat the gas sample 22 within the test cell 12 and/or may be configured to heat the gas sample 22 before entering the test cell 12. For example, at least one of the heaters 30 may heat a body 18 of the test cell 12, and the gas sample 22 may be heated by contacting the body 18 of the test cell 12. Additionally or alternatively, at least one of the heaters 30 may heat a portion of the inlet channel 38 leading to the test cell 12 such that the gas sample 22 heats to the desired temperature as the gas sample 22 passes through the inlet channel 38. Generally, the heaters 30 are resistive heaters but other forms such as radiant heaters or circulating fluid heaters may be used, as recognized by one of skill in the art.

The heaters 30 are configured to heat the gas sample 22 from the temperature of the gas mixture 20 in the measurement volume 42 to the elevated temperature for testing. The elevated temperature is less than the autoignition temperature of the gas sample 22. More specifically, the elevated temperature may be selected based on the autoignition temperature of a stoichiometric mixture of air and a combustion fuel found in the gas sample 22. Flammable mixtures of hydrocarbon fuels may have an autoignition temperature of greater than 150° C., greater than 200° C., or greater than 500° C. For example, flammable methane mixtures have an autoignition temperature of about 600° C., flammable dodecane mixtures have an autoignition temperature of about 200° C., and flammable kerosene fuel mixtures (e.g., jet fuel) have an autoignition temperature of about 200° C. Hence, heaters 30 may be configured to heat the gas sample to an elevated temperature, for example, between 50° C. and 500° C., between 50° C. and 150° C., or between 100° C. and 200° C.

The gas meter 24 of the gas-flammability sensing system 10 is configured to measure one or more physical properties of the gas sample 22 within the test cell 12 when the gas sample 22 is at the elevated temperature. The physical properties are electrical properties, optical properties, and/or intensive thermodynamic properties (relating to the identity, composition, and/or state of molecules rather than the amount of molecules, e.g., normalized by mass, volume, or number of molecules). Generally, the physical properties are intensive properties (relating to the identity, composition, and/or state) or the values are related, normalized, and/or referenced to the value(s) of the same property(ies) measured in a known condition. For example, electrical capacitance (an extensive property) of the gas sample 22 in the test cell 12 may be measured and referenced to the electrical capacitance of a non-flammable gas mixture composed of the same constituents as expected in the gas sample 22.

The gas meter 24 is configured to measure the one or more physical properties to indicate the presence of a combustion reaction in the gas sample 22, the extent of combustion reaction, and/or the type of combustion reaction. Hence, the measured physical properties may be used to indicate and/or predict the flammability of the gas sample 22 and, thus, the gas mixture 20. The measurements may indicate binary results (e.g., presence or absence of reaction and/or flammable mixture) and may indicate quantitative results (e.g., extent of reaction, concentration of combustion fuel). The physical properties may relate to the presence, type, and/or amount of reaction products and/or reaction intermediates.

The gas meter 24 may measure the physical properties as a function of time and/or may indicate a rate of change of the physical properties.

The gas meter 24 may include, and/or may be, an electrical meter 60 configured to measure an electrical property of the gas sample 22 within the test cell 12. The electrical property may include, and/or may be, resistivity, conductivity, permittivity, capacitance, resistance, and/or impedance. The chemical composition changes of the gas sample 22 due to the thermal reaction of the combustion fuel and the oxidant at the elevated temperature may change one or more electrical properties of the gas sample 22. For example, the thermal reaction may generate ionic species such as hydroxide radicals, and ionic species may increase the electrical conductance of the gas sample 22. As another example, the thermal reaction may generate water vapor, and the increase of water vapor may increase the electrical permittivity of the gas sample 22.

The electrical meter 60 may be configured to generate and/or to sense an electric current and/or a voltage. The electric current and/or voltage may be DC (direct current) or AC (alternating current) as suited to measure the resistivity, conductivity, permittivity, capacitance, resistance, and/or impedance. The electrical meter 60 may include, and/or may be, a voltmeter, an ohmmeter, an ammeter, an inductance meter, an impedance meter, and/or a network analyzer.

Electrical properties of the gas sample 22 may be measured by placing the gas sample 22 in the probed region 14 between electrodes 62. The electrodes 62 may be in direct electrical contact with gas sample 22 (e.g., surface 64 of electrodes 62 may contact gas sample 22). In some embodiments, the electrodes 62 may be isolated from the gas sample 22 by a protective layer. The protective layer may be electrically conductive or electrically insulating. The protective layer may be configured to be non-reactive with the gas sample 22. The protective layer may be at the surface 64 and/or the protective layer may be a portion of the body 18 of the test cell 12 (e.g., electrodes 62 may contact the outside of the body 18).

The electrodes 62 may be configured for impedance measurements with the electrodes 62 separated by the gas sample 22 in a known geometry (e.g., within probed region 14). The electrode geometry may be characterized by an effective spacing that is related to the sample thickness 16 of the probed region 14.

Figure 2:
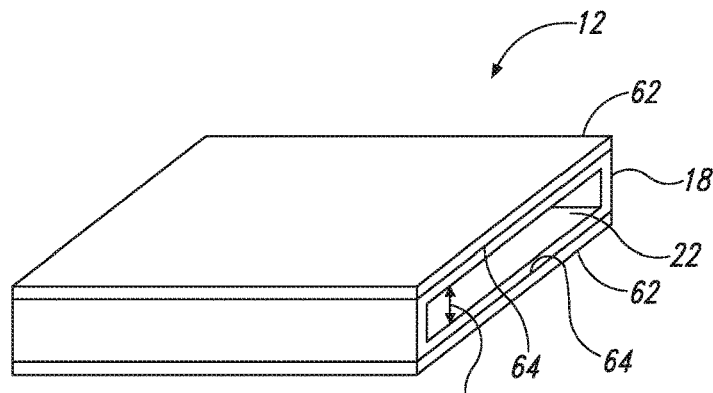
FIG. 2 is an example of a parallel plate electrical test cell for gas-flammability sensing according to the present disclosure.

As shown in FIG. 2, the electrodes 62 may be arranged in a parallel plate arrangement. In the example of FIG. 2, the body 18 has a rectangular profile with an internal dimension that is the sample thickness 16. The body 18 is sufficiently electrically insulating to isolate the electrodes 62. The electrodes 62 contact the outside of the body 18 (i.e., the surfaces 64 contact the body 18 and not the gas sample 22). For capacitive measurements of the gas sample 22 in this parallel plate arrangement, the capacitance of the gas sample 22 is related to the electrical permittivity of the gas sample 22 times the area of the electrodes 62 divided by the sample thickness 16 of the probed region 14. The capacitance may be increased and become generally easier to measure if the area becomes larger and/or the sample thickness 16 becomes smaller. Hence, the probed region 14 may be relatively thin and wide. For example, the electrodes 62 may include two spaced-apart plate electrodes. The plate electrodes may each have a surface area that is at least 10 times the square of the distance between the plate electrodes.

Figure 3:
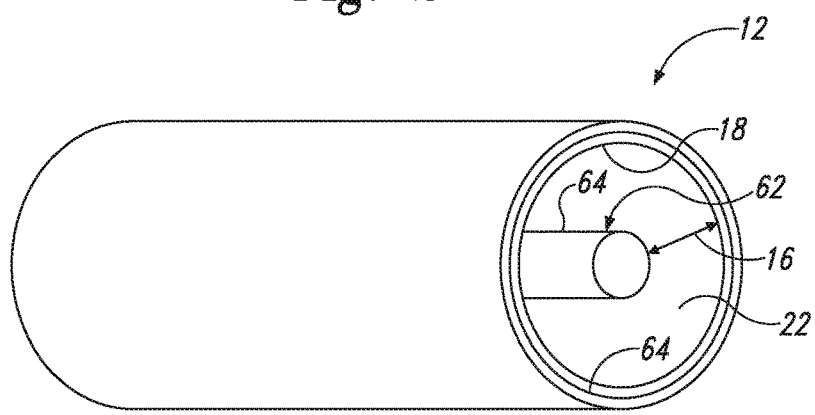
FIG. 3 is an example of a concentric electrical test cell for gas-flammability sensing according to the present disclosure.

As shown in FIG. 3, the electrodes 62 may be arranged concentrically. In the example of FIG. 3, the body 18 is tubular with a circular cross-section. One electrode 62 (the outer electrode) is tubular and contacts the outside of the body 18 (i.e., the surface 64 contacts the body 18). The other electrode 62 (the inner electrode) is cylindrical and arranged within the interior of the body 18. The surface 64 of the interior electrode 62 contacts the gas sample 22 directly. For capacitive measurements of the gas sample 22, the capacitance of the gas sample 22 is related to the electrical permittivity of the gas sample 22 times the length of the concentric electrodes 62 divided by the natural logarithm of the ratio of the outer electrode radius to the inner electrode radius. The capacitance may be increased and become generally easier to measure if the length becomes longer and/or the radius ratio becomes smaller. Hence, the probed region 14 may be relatively thin and long. For example, the electrodes 62 may include two concentric electrodes with a length (i.e., the length of the axis of the concentric electrodes) that is at least 10 times the sample thickness 16 of the gas sample 22 between the electrodes 62.

Figure 4:
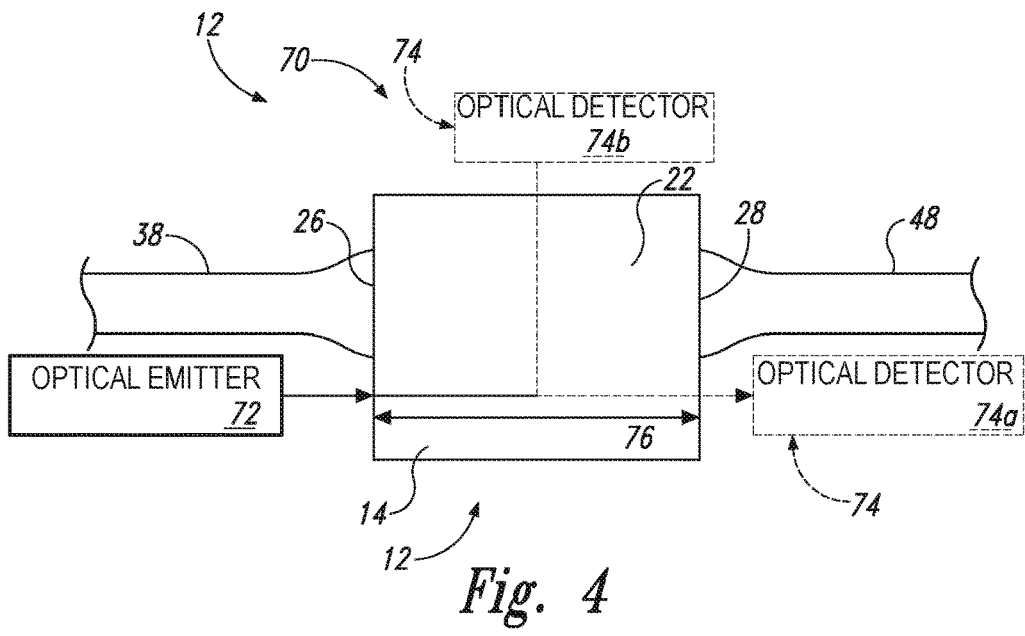
FIG. 4 is an example of an optical test cell configuration in a gas-flammability sensing system according to the present disclosure.

As shown in FIG. 4, the gas meter 24 may include, and/or may be, an optical meter 70 configured to measure an optical property of the gas sample 22 within the test cell. The optical property may include, and/or may be, absorbance, transmittance, scattering, and/or luminescence emission (e.g., fluorescence emission). The chemical composition changes of the gas sample 22 due to the thermal reaction of the combustion fuel and the oxidant at the elevated temperature may change one or more optical properties of the gas sample 22. For example, the thermal reaction may generate water vapor, and the increase of water vapor may increase the optical absorbance of the gas sample 22 at specific wavelengths.

Optical properties of the gas sample 22 may be measured by placing the sample 22 in the probed region 14 in an optical cell. For example, the body 18 may be optically transparent at the wavelength(s) of interest and/or may include optical windows. The optical meter 70 generally includes an optical emitter 72 (e.g., a lamp, a light emitting diode, a laser) and an optical detector 74 (e.g., a photodiode, a camera, a photomultiplier tube). The optical meter 70 may include filters, mirrors, lenses, etc. to direct and/or isolate the light as desired (e.g., to focus light into the optical cell, to isolate emission wavelengths). As used here, the terms optical and light refer to electromagnetic radiation generally within the range from ultraviolet to far infrared (i.e., 50 nm (nanometers) to 20,000 nm).

The optical meter 70 may be arranged to measure light transmitted through the gas sample 22. For example, the optical detector 74*a* may be positioned generally colinearly with the light emitted by the optical emitter 72 and with the probed region 14 between the optical emitter 72 and the optical detector 74*a*. Such an arrangement may be used for transmittance and absorbance measurements. This generally colinear arrangement is characterized by an optical path length 76 that the light travels through. Generally, a longer path length provides for a more sensitive measurement than a shorter path length. The optical path length 76 generally is arranged in a direction other than the sample thickness 16 of the gas sample 22 (which may be relatively small (thin) as described further herein). However, the optical path length 76 may be arranged parallel to the sample thickness 16 in some embodiments.

The optical meter 70 may be arranged to measure light emitted and/or scattered by the gas sample 22. For example, the optical detector 74*b* may be positioned non-colinearly with the light emitted by the optical emitter 72 (e.g., the optical detector 74*b* may observe an orthogonal light path as shown in FIG. 4). Such an arrangement may be used to reduce direct observation of the light emitted from the optical emitter 72 and may be used for fluorescence and scattering measurements.

In some embodiments, the gas meter 24 may include, and/or may be, a gas density meter that is configured to measure the density of the gas sample 22 within the test cell 12. Additionally or alternatively, the gas meter 24 may be configured to measure an intensive thermodynamic property such as density, viscosity, heat capacity, and thermal conductivity using conventional devices as understood by one of skill in the art. For example, gas density may be measured with a vibrating element gas analyzer, a Coriolis meter, etc.

Returning to FIG. 1, the gas-flammability sensing system 10 may include one or more auxiliary detectors 58 that are configured to measure system parameters such as gas temperature, pressure, and/or flow speed. For example, one or more of the auxiliary detectors 58 may be configured to measure the temperature, pressure, and/or flow speed of the gas sample 22 in the inlet channel 38. Additionally or alternatively, one or more of the auxiliary detectors 58 may be configured to measure the temperature, pressure, and/or flow speed of the gas sample in the test cell 12. Auxiliary detectors 58 may be located in the measurement volume 42, at the inlet 40, in the inlet channel 38, at the test cell inlet 26, in the test cell 12, in the probed region 14, at the test cell outlet 28, in the outlet channel 48, and/or at the outlet 50.

The gas-flammability sensing system 10 may include a controller 80 configured, adapted, and/or programmed to control the operation of the gas-flammability sensing system 10 as a whole and/or individual components of the gas-flammability sensing system 10. The controller 80 may be configured, adapted, and/or programmed (a) to measure the physical property or properties of the gas sample 22 with the gas meter 24, (b) to maintain the temperature of the gas sample 22 in the test cell 12 with the heater 30, (c) to collect the gas sample 22 from the measurement volume 42, (d) to discharge the gas sample 22 through the outlet 50, and/or (e) to determine the flammability of the gas mixture 20 in the measurement volume 42 based upon the physical property or properties of the gas sample 22. The controller 80 may be configured and/or programmed to perform any of the methods described herein. The controller 80 may include a computer, an embedded controller, a programmable logic device, and/or a field-programmable gate array. As used herein, where the controller 80 is configured, adapted, and/or programmed to perform a function, the configuration, adaptation, and/or programming may be in the form of hardware (e.g., wiring, digital logic chips), firmware (e.g., field-programmable gate array, embedded code), and/or software.

Figure 5:
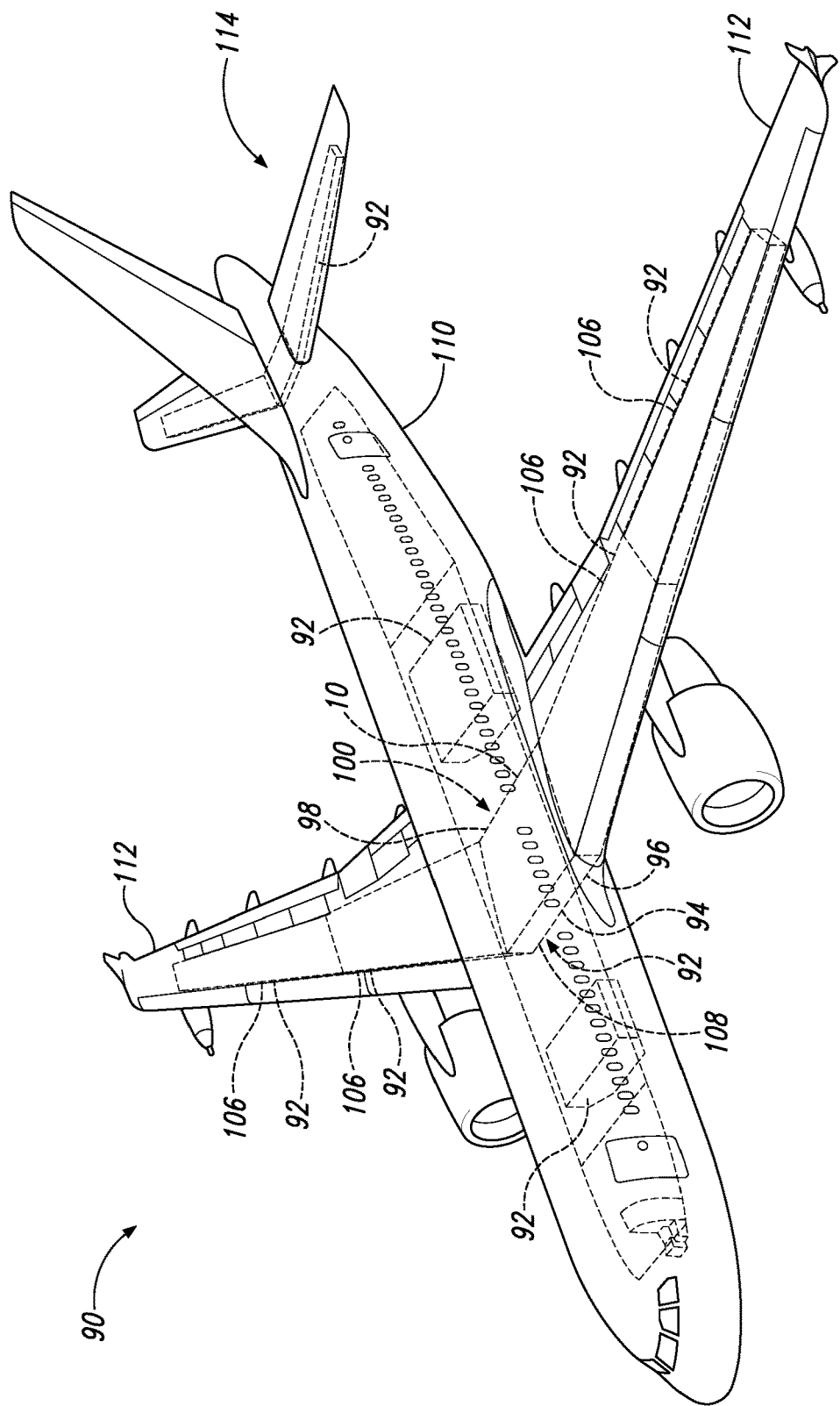
FIG. 5 is a schematic representation of an aircraft according to the present disclosure.

FIG. 5 illustrates and aircraft 90 that may incorporate a gas-flammability sensing system 10. The aircraft 90 includes a fuel tank 92 and the gas-flammability sensing system 10 positioned and configured to measure a flammability of the gas in a ullage space 96 of the fuel tank 92. The gas-flammability sensing system 10 on board aircraft 90 is configured to sample gas from one or more fuel tanks 92. As discussed herein, the gas may be the gas mixture 20 sampled from the ullage space 96 of the fuel tanks 92. Aircraft 90 may have more than one gas-flammability sensing system 10 and may have an individual gas-flammability sensing system 10 for each fuel tank 92. Additionally or alternatively, aircraft 90 may include one or more conventional flammability sensors 98 (e.g., catalytic combustion sensors, infrared absorption sensors, flame ionization sensors, and/or oxygen sensors) configured to sample gas from one or more fuel tanks 92.

Fuel tanks 92 of aircraft 90 may be disposed in various locations such as the fuselage 110, the wings 112, and/or the empennage 114. Many commercial aircraft 90 have fuel tanks 92 in the wings 112 (wing fuel tanks 106) and a center fuel tank 108 in the fuselage 110 between the wings 112.

Fuel 94 may be distributed preferentially to wing fuel tanks 106 over the center fuel tank 108. Hence, the center fuel tank 108 may have a significant portion that is ullage space 96 rather than fuel 94. Generally, the ullage space 96 of fuel tanks 92 on the aircraft 90 may be vented to the atmosphere and the ullage space 96 is exposed to atmospheric conditions (such as air pressure and temperature). The fuel 94 in the fuel tanks 92 may create more or less fuel vapor depending on the pressure and the temperature in the ullage space 96. Conditions in the fuel tanks may include operating and/or storage conditions on the surface of the Earth and at altitude. For example, fuel tanks 92 may experience temperatures between −60° C. and less than 150° C. Generally, the ullage space 96 may experience a temperature range during flight from −40° C. to 50° C. Fuel tanks 92 may experience pressures between 10 kPa (kilopascals) and 120 kPa, corresponding to altitudes of about 15,000 m (meters; about 50,000 feet) and sea level. Generally, the ullage space 96 may experience a pressure range during flight from 30 kPa to 100 kPa (absolute).

Figure 6:
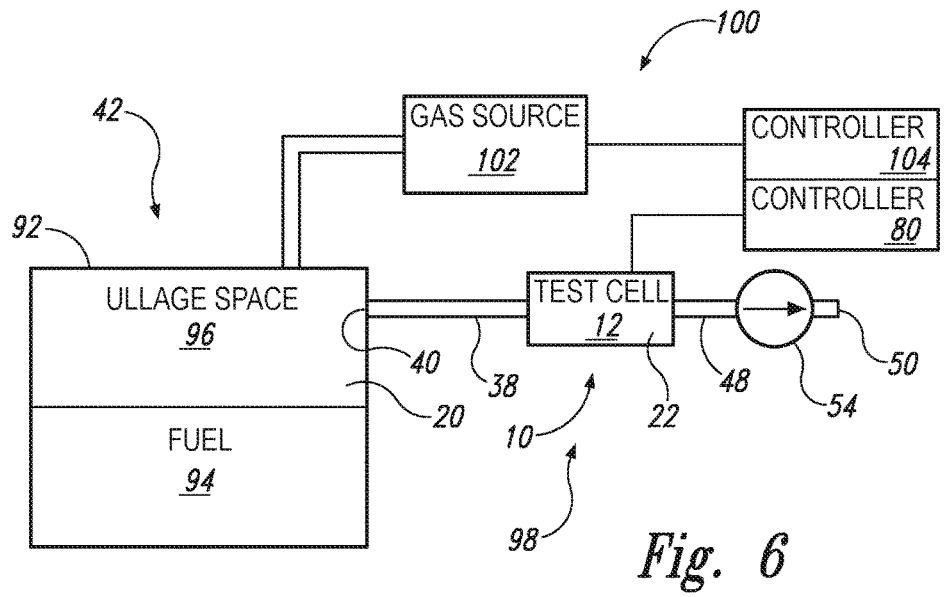
FIG. 6 is a schematic representation of a fuel tank inerting system incorporating a gas-flammability sensor according to the present disclosure.

As shown generally in FIG. 5, aircraft 90 may include a fuel tank inerting system 100. As shown in FIG. 6, the fuel tank inerting system 100 is associated with the fuel tank 92 and includes a gas source 102 and the flammability sensor 98 (which may be the gas-flammability sensing system 10). The fuel tank inerting system 100 may be on board aircraft 90 or may be associated with the fuel tank 92 in other contexts such as a fuel storage facility, a fuel transport container, or a fuel supply (e.g., for a vehicle, power generator, etc.). On board aircraft 90, the fuel tank inerting system 100 may be associated with one or more fuel tanks 92 (for example, the center fuel tank 108). One fuel tank inerting system 100 may serve more than one fuel tank 92. One fuel tank 92 may have one dedicated fuel tank inerting system 100.

The gas source 102 is a source of 'inert' gas for inerting the fuel tank 92. The gas source 102 is configured to supply the inert gas to the ullage space 96 of the fuel tank 92 to dilute and/or displace potentially flammable gas mixture 20 in the ullage space 96. The inert gas supplied is non-flammable and has less oxidant than the target concentration in the ullage space 96 that will produce a non-flammable mixture. The gas source 102 may include a gas reservoir (e.g., a compressed gas cylinder, a cryogenic liquid Dewar container) and/or a gas generation system. For example, the inert gas may be nitrogen-enriched air which may be generated by air separation technologies such as pressure swing adsorption and molecular-selective membranes. On board aircraft 90, the input air for air separation technologies may be engine bleed air (as produced a turbine engine). In pressure swing adsorption, input air is passed through a bed of oxygen-selective adsorbing medium (i.e., molecular sieve material such as zeolite). The air that passes through the adsorbing medium is depleted of oxygen (enriched in nitrogen). The adsorbing medium needs to be periodically purged of adsorbed oxygen. In substantially continuous flow apparatuses, two adsorbing medium beds typically are used, with one filtering input air while the other is purged of adsorbed oxygen. With molecular-selective membranes, the input air constituents are separated generally based on the molecular permeability of the membrane, size of the molecules, and/or molecular weight of the molecules. Molecular-selective membranes may discriminate between molecular nitrogen and molecular oxygen. Examples of molecular-selective membranes include polymers, silicone (e.g., polydimethylsiloxane), ceramics, and combination materials.

The fuel tank inerting system 100 includes a controller 104 that is configured, adapted, and/or programmed to operate the gas source 102 to supply inert gas in the amounts needed to maintain a non-flammable environment in the ullage space 96. The flammability of the gas mixture 20 in the ullage space 96 is monitored by the flammability sensor 98. The controller 104 is configured, adapted, and/or programmed to determine the amount and/or timing of introduction of the inert gas based on the measured flammability of the gas mixture 20 in the ullage space 96. Inert gas may be supplied as one or more bursts of gas that provide the desired amount and/or rate of gas flow.

Generally, as the gas mixture 20 approaches the flammability range, more inert gas is added and/or more of the gas mixture 20 is vented out of the ullage space 96. As the gas mixture 20 recedes from the flammability range, less inert gas may be added and/or less of the gas mixture 20 may be vented out of the ullage space 96. Inert gas may be added in an amount and/or at a rate related to the flammability of the gas mixture 20, the amount of fuel 94, the volume of the ullage space 96, the pressure in the ullage space 96, the temperature in the ullage space 96, the rate of change of any of the foregoing, and/or the projected value and/or rate of change of any of the foregoing. For example, the controller 104 may be configured, adapted, and/or programmed to supply inert gas to the fuel tank 92 of the aircraft 90 when the aircraft 90 is descending (and therefore projected to experience an air pressure increase and consequent increase in oxygen). As discussed further herein, the flammability of the gas mixture 20 may include whether the gas mixture 20 is flammable (a binary indicator) and may include a measure of how close the gas mixture 20 is to the flammability range (e.g., a concentration of oxygen relative to the oxygen concentration at the appropriate flammability limit).

The gas source 102 may be configured and the controller 104 may be configured, adapted, and/or programmed to generate inert gas at a rate in accord with the average expected needs of the fuel tank 92 and to store excess generated gas as a buffer for when the need of the fuel tank 92 exceeds generation rate of the gas source 102.

The controller 104 may include the controller 80, and/or the controller 104 may communicate with the controller 80. The controller 104 may be configured and/or programmed to perform any of the methods described herein. The controller 104 may include a computer, an embedded controller, a programmable logic device, and/or a field-programmable gate array. As used herein, where the controller 104 is configured, adapted, and/or programmed to perform a function, the configuration, adaptation, and/or programming may be in the form of hardware (e.g., wiring, digital logic chips), firmware (e.g., field-programmable gate array, embedded code), and/or software.

Figure 7:
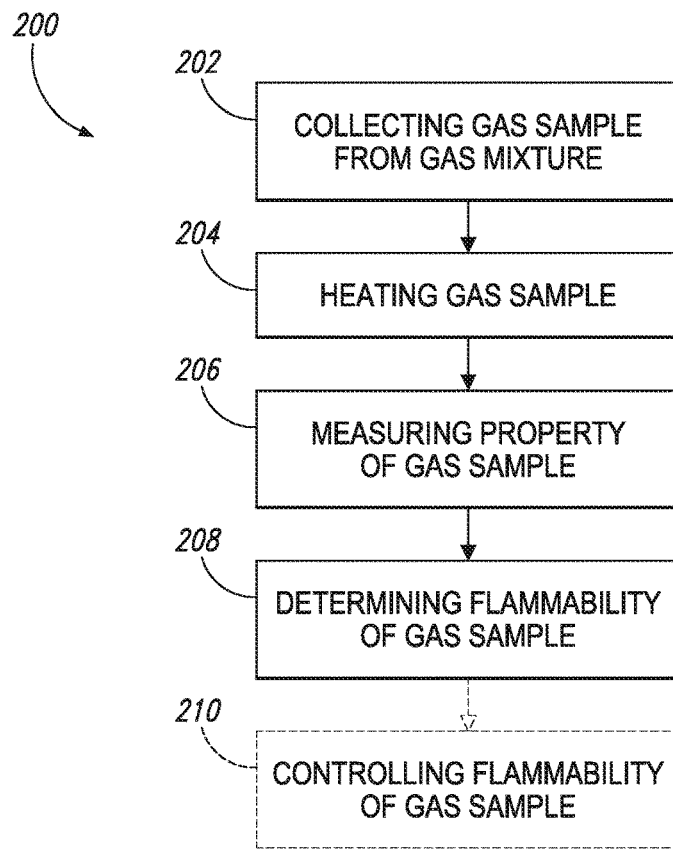
FIG. 7 is a schematic representation of gas-flammability sensing methods according to the present disclosure.

FIG. 7 schematically illustrates methods 200 according to the present disclosure. Methods 200 may be methods of determining the flammability of a gas sample (such as gas sample 22) from a gas mixture (such as gas mixture 20) in a measurement volume (such as measurement volume 42). Methods 200 may be methods of controlling the flammability of the gas mixture in the measurement volume. In general, methods 200 may include using one more of the gas-flammability sensing system 10, the aircraft 90, the fuel tank inerting system 100, and/or components thereof.

Methods 200 include collecting 202 the gas sample from the gas mixture in the measurement volume and determining 208 the flammability of the gas mixture in the measurement volume based upon a physical property of the gas sample. Methods 200 may include heating 204 the gas sample to an elevated temperature below the autoignition temperature of the gas sample, measuring 206 the physical property of the gas sample after the gas sample is heated, and controlling 210 the flammability of the gas mixture based upon the measured flammability. Methods 200 may include repeating the collecting 202, the heating 204, the measuring 206, the determining 208, and/or the controlling 210 with another gas sample from the measurement volume. Repeating may be performed to monitor and/or to control the flammability of the gas mixture in the measurement volume. Generally, methods 200 are performed without exposing the gas mixture or the gas sample(s) to any ignition source (such as a flame, a spark, or a temperature above the autoignition temperature).

Collecting 202 may include sampling the gas mixture in an open or an enclosed volume (such as a fuel tank, e.g., fuel tank 92). In a fuel tank, collecting may include sampling the gas mixture from the ullage space (e.g., ullage space 96). The fuel tank may be a fuel tank (e.g., fuel tank 92) on board an aircraft (e.g., aircraft 90) and/or may be a center fuel tank (e.g., center fuel tank 108) of the aircraft. Collecting 202 may include drawing the gas sample into a test cell (e.g., test cell 12) of a gas-flammability sensing system (e.g., gas-flammability sensing system 10).

Heating 204 may include heating the sample to cause thermal reaction of the gas sample. The thermal reaction is the same reaction as may occur during rapid combustion but does not exhibit a flame front, self-propagating combustion, or self-sustaining combustion. The elevated temperature is a temperature below the autoignition temperature of the gas sample (and the gas mixture) and generally is selected to be below the autoignition temperature of any expected gas mixture that might be sampled during any repeated collecting and/or heating. Selecting the same temperature for repeated operations may enable a high repetition rate and/or simplify the heating control. The elevated temperature may be selected based on the autoignition temperature of a stoichiometric mixture of air (or an oxidant gas) and a combustion fuel found in the gas sample. For example, the gas mixture may include hydrocarbon fuel vapor, which, as discussed herein, may have an autoignition temperature of greater than 150° C., greater than 200° C., or greater than 500° C. Heating 204 may include heating to an elevated temperature between 50° C. and 500° C., between 50° C. and 150° C., or between 100° C. and 200° C. For example, the elevated temperature may be at least 50° C., at least 100° C., at least 150° C., at most 800° C., at most 500° C., at most 200° C., at most 150° C., and/or at most 100° C.

Heating 204 may include heating the gas sample in a manner to avoid igniting the gas sample and/or the gas mixture. For example, the gas sample may be heated in a test cell (such as test cell 12) that is configured to quench a propagating flame front in the gas sample, e.g., the sample thickness of the probed region in the test cell is less than the relevant characteristic quenching dimension (e.g., the quenching distance) of a mixture of the corresponding combustion fuel and air (or a mixture of the corresponding combustion fuel and oxidant (e.g., molecular oxygen)). As another example, methods 200 may include separating the gas sample from the gas mixture by a flame arrester (e.g., flame arrester 34) prior to heating 204. Hence, if the gas sample is ignited during heating 204, the flame front would be quenched by the flame arrester and would not propagate to the gas mixture to ignite the gas mixture.

The physical property obtained by measuring 206 and used by determining 208 is a physical property related to the chemical composition of the heated gas sample and indicate the combustion state of the gas sample, as discussed herein. The physical property may indicate and/or relate to the presence of a combustion reaction in the gas sample, the extent of combustion reaction, and/or the type of combustion reaction. The physical property may relate to the presence, type, and/or amount of reaction products, and/or reaction intermediates.

The physical property may be an electrical property, an optical property, and/or an intensive thermodynamic property. The physical property may relate directly to the identity, composition, and/or state of the gas sample. The physical property values may be related, normalized, and/or referenced to the same physical property measured in a known condition (e.g., with a reference gas, at a reference temperature, etc.). Examples of electrical properties include resistivity, conductivity, permittivity, capacitance, resistance, and impedance. Electrical properties may be AC or DC properties. Examples of optical properties include absorbance, transmittance, scattering, and/or luminescence emission (e.g., fluorescence emission). Intensive thermodynamic properties include density, viscosity, heat capacity, and thermal conductivity. Physical properties may be measured as described with respect to the test cell 12 and the gas meter 24. For example, capacitance may be measured with parallel or concentric electrodes that have the gas sample between.

Measuring 206 may include repeatedly measuring the physical property of the gas sample at the elevated temperature, e.g., to determine a rate of the thermal reaction in the gas sample. Methods 200 may include measuring the physical property of the gas sample during heating 204 in a manner the same or similar to measuring 206 (performed after heating 204). The measurement of the physical property during heating 204 may be used to determine a temperature relation of the physical property (e.g., a threshold temperature, a temperature response rate, etc.). Methods 200 may include measuring the physical property of the gas sample before heating 204 in a manner the same or similar to measuring 206 (performed after heating 204). The measurement of the physical property before heating 204 provides a pre-heating value and the measurement of the physical property after heating 204 provides a post-heating value. Methods 200 (e.g., determining 208) may include comparing the pre-heating value and the post-heating value, for example to obtain difference, an average, a rate of change, etc.

Determining 208 the flammability of the gas mixture based on the measured physical property of the gas sample generally includes relating the physical property to the flammability range of combustion fuel that may be in the gas sample. However, determining 208 may include determining whether the gas sample is flammable without knowledge of any combustion fuel in the gas sample and/or the gas mixture.

The flammability of the gas mixture may be a binary value (or determination) corresponding to a flammable or a non-flammable gas mixture. Flammability may be determined by comparing the measured physical property (or related quantity such as rate of change, normalized value, etc.) to a threshold value. If the measured physical property (or related quantity) meets the threshold (e.g., according to the circumstances, the value is greater than, less than, or equal to the threshold), then the gas mixture may be determined to be flammable. Alternatively expressed, the flammability may be determined to be positive. For example, the flammability of the gas mixture may be determined to be positive if the measured physical property value corresponds to a concentration of combustion fuel in the gas sample that is at least as great as the lower flammability limit of the combustion fuel in air (or in a binary mixture of the combustion fuel and molecular oxygen). As another example, the flammability of the gas mixture may be determined to be negative if the measured physical property value corresponds to a concentration of oxygen in the gas sample that is less than a known flammability threshold for sustained combustion of a combustion fuel mixture. As yet another example, the flammability of the gas mixture may be determined to be positive if the measured physical property value (or related quantity) indicates a thermal reaction rate greater than a threshold value.

The flammability of the gas mixture may be more than a binary value and may indicate the extent of flammability (e.g., how close the gas mixture is to the flammability range) and/or the likelihood of flammability in the given conditions. For example, the measure physical property value (or related quantity) may correspond to combustion fuel concentration and/or oxidant (e.g., oxygen) concentration in the gas sample. The flammability may be expressed as the corresponding concentration, the relative concentration as compared to the appropriate flammability limit. For example, the flammability may be expressed as a fraction of the lower flammability limit of the combustion fuel in air (or in a binary mixture of the combustion fuel and molecular oxygen).

Methods 200 may include controlling 210 the flammability of the gas mixture by providing more or less 'inert' gas to the measurement volume according to the measured flammability, the measured physical property, and/or a quantity related thereto (e.g., a rate of change, maximum, an average). Inert gas is not necessarily completely inert and may include oxidant, as discussed herein with respect to the process of inertion and the fuel tank inerting system 100. Controlling 210 may include controlling a concentration of the inert gas and/or a concentration of oxidant (e.g., oxygen) in the measurement volume (e.g., the ullage space of the fuel tank).

Examples of inventive subject matter according to the present disclosure are described in the following enumerated paragraphs.

A1. A gas-flammability sensing system comprising:
an inlet;
an outlet;
a test cell fluidically connected to the inlet and the outlet, and structured to receive a gas sample through the inlet and to discharge the gas sample through the outlet;
a heater in thermal communication with the test cell, wherein the heater is positioned and configured to heat the gas sample within the test cell to between 50° C. and 500° C.; and
a gas meter configured to measure a physical property of the gas sample within the test cell related to a combustion state of the gas sample in the test cell.

A2. The gas-flammability sensing system of paragraph A1, wherein the gas meter is an electrical meter configured to measure an electrical property of the gas sample within the test cell related to the combustion state of the gas sample in the test cell.

A2.1. The gas-flammability sensing system of paragraph A2, wherein the electrical property includes at least one of resistivity, conductivity, permittivity, capacitance, resistance, and impedance.

A2.2. The gas-flammability sensing system of any of paragraphs A2-A2.1, wherein the test cell includes a plurality of electrodes and defines a probed region for the gas sample that is between at least two of the plurality of electrodes.

A2.2.1. The gas-flammability sensing system of paragraph A2.2, wherein the at least two of the plurality of electrodes are plate electrodes that each have a surface with an area that is at least 10 times a squared value of a distance between the plate electrodes.

A2.2.2. The gas-flammability sensing system of paragraph A2.2, wherein the at least two of the plurality of electrodes are arranged concentrically and optionally wherein a length of the at least two of the plurality of electrodes is at least 10 times a sample thickness of a probed region of the test cell between the at least two of the plurality of electrodes.

A3. The gas-flammability sensing system of paragraph A1, wherein the gas meter is an optical meter configured to measure an optical property of the gas sample within the test cell related to a combustion state of the gas sample in the test cell.

A3.1. The gas-flammability sensing system of paragraph A3, wherein the optical property includes at least one of absorbance, transmittance, scattering, luminescence emission, and fluorescence emission.

A4. The gas-flammability sensing system of paragraph A1, wherein the gas meter is a gas density meter configured to measure a density of the gas within the test cell.

A5. The gas-flammability sensing system of any of paragraphs A1-A4, wherein the gas meter is configured to measure an intensive thermodynamic property that includes at least one of density, viscosity, heat capacity, and thermal conductivity.

A6. The gas-flammability sensing system of any of paragraphs A1-A5, wherein the gas meter is configured to quantify at least one of an amount of a combustion product and an extent of combustion.

A7. The gas-flammability sensing system of any of paragraphs A1-A6, wherein the gas sample includes a combustion fuel and wherein the heater is positioned and configured to heat the gas sample to a temperature below an autoignition temperature of a stoichiometric mixture of air and the combustion fuel of the gas sample.

A8. The gas-flammability sensing system of any of paragraphs A1-A7, wherein the heater is positioned and configured to heat the gas sample within the test cell to at least 100° C., at most 150° C., and/or at most 200° C.

A9. The gas-flammability sensing system of any of paragraphs A1-A8, wherein the temperature of the test cell is between 50° C. and 500° C.

A9.1. The gas-flammability sensing system of paragraph A9, wherein the temperature of the test cell is at least 100° C., at most 150° C., and/or at most 200° C.

A10. The gas-flammability sensing system of any of paragraphs A1-A9.1, wherein the gas sample includes a/the combustion fuel, wherein the test cell has a probed region with a sample thickness for the gas sample that is configured to quench a propagating flame front in the gas sample and optionally is less than a characteristic quenching dimension of a mixture of the combustion fuel and air.

A11. The gas-flammability sensing system of any of paragraphs A1-A10, wherein the test cell has a probed region with a sample thickness for the gas sample that is at most 10 mm, at most 5 mm, at most 2 mm, at most 1 mm, and/or at least 0.1 mm.

A12. The gas-flammability sensing system of any of paragraphs A1-A11, further comprising a pump in fluidic communication with the test cell and configured to pump the gas sample.

A12.1. The gas-flammability sensing system of paragraph A12, wherein the pump is configured to exhaust the gas sample from the test cell to the outlet.

A12.2. The gas-flammability sensing system of any of paragraphs A12-A12.1, wherein the pump is configured to draw the gas sample from the inlet to the test cell.

A13. The gas-flammability sensing system of any of paragraphs A1-A12.2, wherein the inlet is fluidically connected to a measurement volume to sample gas contents of the measurement volume.

A13.1. The gas-flammability sensing system of paragraph A13, wherein the measurement volume is a ullage space of a fuel tank.

A13.2. The gas-flammability sensing system of any of paragraphs A13-A13.1, wherein the gas-flammability sensing system is structured for continuous sampling of the gas contents from the measurement volume.

A13.3. The gas-flammability sensing system of any of paragraphs A13-A13.2, further comprising a flame arrester between the measurement volume and the test cell.

A14. The gas-flammability sensing system of any of paragraphs A1-A13.3, wherein the test cell is structured for continuous flow of the gas sample through the test cell.

A15. The gas-flammability sensing system of any of paragraphs A1-A14, further comprising a sample valve configured to selectively permit the gas sample to flow from the inlet to the test cell.

A16. The gas-flammability sensing system of any of paragraphs A1-A15, further comprising an exit valve configured to selectively permit the gas sample to flow from the test cell to the outlet.

A17. The gas-flammability sensing system of any of paragraphs A1-A16, further comprising an inlet channel that connects the inlet to a test cell inlet of the test cell.

A17.1. The gas-flammability sensing system of paragraph A17, wherein the inlet channel is configured to thermally isolate the test cell from the inlet.

A17.2. The gas-flammability sensing system of any of paragraphs A17-A17.1, further comprising an inlet auxiliary detector configured to measure at least one of a temperature, a pressure, and a flow speed of the gas sample in the inlet channel.

A17.3. The gas-flammability sensing system of any of paragraphs A17-A17.2, further comprising a flame arrester within the inlet channel.

A18. The gas-flammability sensing system of any of paragraphs A1-A17.3, further comprising an outlet channel that connects the outlet to a test cell outlet of the test cell.

A19. The gas-flammability sensing system of any of paragraphs A1-A18, further comprising an auxiliary detector configured to measure at least one of a temperature, a pressure, and a flow speed of the gas sample in the test cell.

A20. The gas-flammability sensing system of any of paragraphs A1-A19, wherein the gas-flammability sensing system includes no ignition sources.

A21. The gas-flammability sensing system of any of paragraphs A1-A20, further comprising the gas sample in the test cell.

A22. The gas-flammability sensing system of any of paragraphs A1-A21, further comprising a controller programmed to perform any of the methods of paragraphs C1-C14.

B1. An aircraft comprising:
a fuel tank with a ullage space; and
a gas-flammability sensing system positioned and configured to measure a flammability of gas in the ullage space of the fuel tank.

B2. The aircraft of paragraph B1, wherein the gas-flammability sensing system is the gas-flammability sensing system of any of paragraphs A1-A22.

B3. The aircraft of any of paragraphs B1-B2, further comprising a fuel tank inerting system and a controller, wherein the fuel tank inerting system is configured to supply inert gas into the ullage space of the fuel tank, and wherein the controller is programmed to control the amount of inert gas supplied to the ullage space based upon the flammability of the gas in the ullage space.

B3.1. The aircraft of paragraph B3, wherein the controller is programmed to perform any of the methods of the paragraphs C1-C14.

B4. The aircraft of any of paragraphs B1-B3.1, further comprising at least one of a fuselage, a wing, an empennage.

B5. The aircraft of any of paragraphs B1-B4, wherein the fuel tank is a center fuel tank.

C1. A method of determining a flammability of a gas sample, the method comprising:
collecting a gas sample from a gas mixture in a measurement volume;
heating the gas sample to between 50° C. and 500° C.;
after heating, measuring a physical property of the gas sample related to a combustion state of the gas sample; and
determining a flammability of the gas mixture in the measurement volume based upon the physical property of the gas sample.

C2. The method of paragraph C1, wherein the gas sample is a first gas sample and the method further comprises repeating the collecting, heating, and measuring with a second gas sample.

C3. The method of any of paragraphs C1-C2, wherein collecting includes collecting the gas sample from a ullage space of a fuel tank.

C3.1. The method of paragraph C3, further comprising controlling a concentration of inert gas in the ullage space based upon the flammability of the gas mixture, and optionally controlling the concentration of the inert gas based upon at least one of a level of the flammability of the gas and a rate of change of the flammability of the gas mixture.

C3.2. The method of any of paragraphs C3-C3.1, wherein the fuel tank is an aircraft fuel tank, optionally a center fuel tank of an aircraft.

C4. The method of any of paragraphs C1-C3.2, wherein the physical property of the gas sample is an electrical property of the gas sample.

C4.1. The method of paragraph C4, wherein the electrical property includes at least one of resistivity, conductivity, permittivity, capacitance, resistance, and impedance.

C5. The method of any of paragraphs C1-C3.2, wherein the physical property of the gas sample is an optical property of the gas sample.

C5.1. The method of paragraph C5, wherein the optical property includes at least one of absorbance, transmittance, scattering, luminescence emission, and fluorescence emission.

C6. The method of any of paragraphs C1-C3.2, wherein the physical property of the gas sample is an intensive thermodynamic property of the gas sample that includes at least one of density, viscosity, heat capacity, and thermal conductivity.

C7. The method of any of paragraphs C1-C6, wherein the gas sample includes a combustion fuel.

C7.1. The method of paragraph C7, wherein the flammability of the gas mixture is positive if a concentration of the combustion fuel in the gas sample is at least as great as a lower flammability limit of the combustion fuel in air.

C7.2. The method of any of paragraphs C7-C7.1, wherein the flammability of the gas mixture is positive if a concentration of the combustion fuel in the gas sample is at least as great as a lower flammability limit of a binary mixture of the combustion fuel and molecular oxygen.

C7.3. The method of paragraph C7, wherein the flammability of the gas mixture is expressed as a fraction of a lower flammability limit of the combustion fuel in air.

C7.4. The method of paragraph C7, wherein the flammability of the gas mixture is expressed as a fraction of a lower flammability limit of a binary mixture of the combustion fuel and molecular oxygen.

C7.5. The method of any of paragraphs C7-C7.4, wherein heating includes heating the gas sample to a temperature below an autoignition temperature of a stoichiometric mixture of air and the combustion fuel of the gas sample.

C7.6. The method of any of paragraphs C7-C7.5, wherein heating includes heating the gas sample to a measurement temperature within a test cell that has probed region with a sample thickness for the gas sample that is configured to quench a propagating flame front in the gas sample and optionally that is less than a characteristic quenching dimension of a mixture of the combustion fuel and air.

C8. The method of any of paragraphs C1-C7.6, wherein heating includes heating the gas sample to at least 100° C., at most 150° C., and/or at most 200° C.

C9. The method of any of paragraphs C1-C8, further comprising measuring the physical property of the gas sample before heating to obtain a pre-heating value, wherein measuring the physical property of the gas sample after heating includes obtaining a post-heating value.

C9.1. The method of paragraph C9, wherein determining the flammability of the gas mixture includes comparing the pre-heating value and the post-heating value.

C10. The method of any of paragraphs C1-C9.1, wherein the flammability indicates a concentration of molecular oxygen in the gas sample.

C11. The method of any of paragraphs C1-C10, further comprising controlling flow of the gas sample from the fuel tank with a pump.

C12. The method of any of paragraphs C1-C11, further comprising drawing the gas sample from the fuel tank into a test cell.

C12.1. The method of paragraph C12, wherein drawing includes drawing the gas sample into a probed region of the test cell.

C12.2. The method of any of paragraphs C12-C12.1, wherein drawing includes drawing the gas sample into the test cell with a pump.

C12.3. The method of any of paragraphs C12-C12.2, wherein drawing includes drawing the gas sample through a flame arrester into the test cell.

C12.4. The method of any of paragraphs C12-C12.3, wherein heating includes heating the gas sample in the test cell.

C12.5. The method of any of paragraphs C12-C12.4, wherein measuring includes measuring the physical property in the test cell.

C13. The method of any of paragraphs C1-C12.5, further comprising isolating the gas sample from the gas mixture in the ullage space of the fuel tank, prior to the heating.

C14. The method of any of paragraphs C1-C13, further comprising isolating the gas sample from the gas mixture in the ullage space of the fuel tank with a flame arrester.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entities in the list of entities, and is not limited to at least one of each and every entity specifically listed within the list of entities. For example, "at least one of A and B" (or, equivalently, "at least one of A or B," or, equivalently, "at least one of A and/or B") may refer to A alone, B alone, or the combination of A and B.

As used herein, the singular forms "a", "an" and "the" may be intended to include the plural forms as well, unless the context clearly indicates otherwise.

The various disclosed elements of systems and steps of methods disclosed herein are not required of all systems and methods according to the present disclosure, and the present disclosure includes all novel and non-obvious combinations and subcombinations of the various elements and steps disclosed herein. Moreover, any of the various elements and steps, or any combination of the various elements and/or steps, disclosed herein may define independent inventive subject matter that is separate and apart from the whole of a disclosed system or method. Accordingly, such inventive subject matter is not required to be associated with the specific systems and methods that are expressly disclosed herein, and such inventive subject matter may find utility in systems and/or methods that are not expressly disclosed herein.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A gas-flammability sensing system comprising:
an inlet;
an outlet;
a test cell fluidically connected to the inlet and the outlet, the test cell structured to receive a gas sample through the inlet and to discharge the gas sample through the outlet;
a heater in thermal communication with the test cell, wherein the heater is positioned and configured to heat the gas sample within the test cell to between 50° C. and 500° C.; and
a gas meter configured to measure a physical property of the gas sample within the test cell related to a combustion state of the gas sample in the test cell;
wherein the gas sample includes a combustion fuel, wherein the test cell has a sample thickness for the gas sample that is configured to quench a propagating flame front in the gas sample and is less than a quenching distance of a mixture of the combustion fuel and air.

2. The gas-flammability sensing system of claim 1, wherein the gas meter is an electrical meter configured to measure an electrical property of the gas sample within the test cell related to the combustion state of the gas sample in the test cell.

3. The gas-flammability sensing system of claim 2, wherein the electrical property includes at least one of resistivity and permittivity.

4. The gas-flammability sensing system of claim 2, wherein the test cell includes a plurality of electrodes and defines a probed region for the gas sample that is between at least two of the plurality of electrodes.

5. The gas-flammability sensing system of claim 4, wherein the at least two of the plurality of electrodes are plate electrodes that each have a surface with an area that is at least 10 times a squared value of a distance between the plate electrodes.

6. The gas-flammability sensing system of claim 4, wherein the at least two of the plurality of electrodes are arranged concentrically and wherein a length of the at least two of the plurality of electrodes is at least 10 times a sample thickness of a probed region of the test cell between the at least two of the plurality of electrodes.

7. The gas-flammability sensing system of claim 1, wherein the gas meter is an optical meter configured to measure an optical property of the gas sample within the test cell related to a combustion state of the gas sample in the test cell, wherein the optical property includes at least one of absorbance, transmittance, scattering, luminescence emission, and fluorescence emission.

8. The gas-flammability sensing system of claim 1, wherein the gas meter is a gas density meter configured to measure a density of the gas sample within the test cell.

9. The gas-flammability sensing system of claim 1, wherein the heater is positioned and configured to heat the gas sample within the test cell to at most 150° C.

10. The gas-flammability sensing system of claim 1, wherein the inlet is fluidically connected to a measurement volume to sample gas contents of the measurement volume, wherein the measurement volume is a ullage space of a fuel tank.

11. The gas-flammability sensing system of claim 1, further comprising:
   an inlet channel that connects the inlet to a test cell inlet of the test cell; and
   a flame arrester within the inlet channel.

12. The gas-flammability sensing system of claim 1, further comprising a pump in fluidic communication with the test cell and configured to pump the gas sample, the pump being configured to draw the gas sample from the inlet to the test cell.

13. An aircraft comprising:
   a fuel tank with a ullage space; and
   the gas-flammability sensing system of claim 1 positioned and configured to measure a flammability of gas in the ullage space of the fuel tank.

14. The aircraft of claim 13, further comprising a fuel tank inerting system and a controller, wherein the fuel tank inerting system is configured to supply inert gas into the ullage space of the fuel tank, and wherein the controller is programmed to control the amount of inert gas supplied to the ullage space based upon the flammability of the gas in the ullage space.

15. The gas-flammability sensing system of claim 1, further comprising a fuel tank with a ullage space, wherein the inlet is in fluidic communication with the ullage space of the fuel tank.

16. The gas-flammability sensing system of claim 15, further comprising a fuel tank inerting system and a controller, wherein the fuel tank inerting system is configured to supply inert gas into the ullage space of the fuel tank, and wherein the controller is programmed to control the amount of inert gas supplied to the ullage space based upon the flammability of the gas in the ullage space.

17. The gas-flammability sensing system of claim 15, wherein the fuel tank is an aircraft fuel tank.

18. The gas-flammability sensing system of claim 15, wherein the gas-flammability sensing system is structured for continuous sampling of gas contents from the ullage space.

19. The gas-flammability sensing system of claim 1, wherein the test cell has a probed region with a sample thickness for the gas sample that is at most 10 mm.

20. The gas-flammability sensing system of claim 1, wherein the gas-flammability sensing system includes no ignition sources.

21. A gas-flammability sensing system comprising:
   an inlet;
   an outlet;
   a test cell fluidically connected to the inlet and the outlet, the test cell structured to receive a gas sample through the inlet and to discharge the gas sample through the outlet;
   a heater in thermal communication with the test cell, wherein the heater is positioned and configured to heat the gas sample within the test cell to between 50° C. and 500° C.;
   a gas meter configured to measure a physical property of the gas sample within the test cell related to a combustion state of the gas sample in the test cell; and
   a fuel tank with a ullage space, wherein the inlet is in fluidic communication with the ullage space of the fuel tank.

22. The gas-flammability sensing system of claim 21, wherein the gas meter is an electrical meter configured to measure an electrical property of the gas sample within the test cell related to the combustion state of the gas sample in the test cell.

23. The gas-flammability sensing system of claim 22, wherein the electrical property includes at least one of resistivity and permittivity.

24. The gas-flammability sensing system of claim 22, wherein the test cell includes a plurality of electrodes and defines a probed region for the gas sample that is between at least two of the plurality of electrodes.

25. The gas-flammability sensing system of claim 24, wherein the at least two of the plurality of electrodes are plate electrodes that each have a surface with an area that is at least 10 times a squared value of a distance between the plate electrodes.

26. The gas-flammability sensing system of claim 24, wherein the at least two of the plurality of electrodes are arranged concentrically and wherein a length of the at least two of the plurality of electrodes is at least 10 times a sample thickness of a probed region of the test cell between the at least two of the plurality of electrodes.

27. The gas-flammability sensing system of claim 21, wherein the gas meter is an optical meter configured to measure an optical property of the gas sample within the test cell related to a combustion state of the gas sample in the test cell, wherein the optical property includes at least one of absorbance, transmittance, scattering, luminescence emission, and fluorescence emission.

28. The gas-flammability sensing system of claim 21, wherein the gas meter is a gas density meter configured to measure a density of the gas sample within the test cell.

29. The gas-flammability sensing system of claim 21, wherein the heater is positioned and configured to heat the gas sample within the test cell to at most 150° C.

30. The gas-flammability sensing system of claim 21, wherein the gas sample includes a combustion fuel, wherein the test cell has a sample thickness for the gas sample that is configured to quench a propagating flame front in the gas sample and is less than a quenching distance of a mixture of the combustion fuel and air.

31. The gas-flammability sensing system of claim 21, wherein the inlet is fluidically connected to a measurement volume to sample gas contents of the measurement volume, wherein the measurement volume is a ullage space of a fuel tank.

32. The gas-flammability sensing system of claim 21, further comprising:
   an inlet channel that connects the inlet to a test cell inlet of the test cell; and
   a flame arrester within the inlet channel.

33. The gas-flammability sensing system of claim 21, further comprising a pump in fluidic communication with the test cell and configured to pump the gas sample, the pump being configured to draw the gas sample from the inlet to the test cell.

34. The gas-flammability sensing system of claim 21, further comprising a fuel tank inerting system and a controller, wherein the fuel tank inerting system is configured to supply inert gas into the ullage space of the fuel tank, and wherein the controller is programmed to control the amount of inert gas supplied to the ullage space based upon the flammability of the gas in the ullage space.

35. The gas-flammability sensing system of claim 21, wherein the fuel tank is an aircraft fuel tank.

36. The gas-flammability sensing system of claim 21, wherein the gas-flammability sensing system is structured for continuous sampling of gas contents from the ullage space.

37. The gas-flammability sensing system of claim 21, wherein the test cell has a probed region with a sample thickness for the gas sample that is at most 10 mm.

38. The gas-flammability sensing system of claim 21, wherein the gas-flammability sensing system includes no ignition sources.

* * * * *